US00PP24129P3

(12) United States Plant Patent
Apps

(10) Patent No.: US PP24,129 P3
(45) Date of Patent: Dec. 31, 2013

(54) DAYLILY PLANT NAMED 'CENTERTON ONE'

(50) Latin Name: *Hemerocallis hybrida*
Varietal Denomination: Centerton One

(75) Inventor: Darrel A. Apps, Wild Rose, WI (US)

(73) Assignee: Blewline Nursery, Inc., Bridgeton, NJ (US)

( * ) Notice: Subject to any disclaimer, the term of this patent is extended or adjusted under 35 U.S.C. 154(b) by 250 days.

(21) Appl. No.: 13/137,569

(22) Filed: Aug. 26, 2011

(65) Prior Publication Data

US 2013/0055480 P1 Feb. 28, 2013

(51) Int. Cl.
*A01H 5/00* (2006.01)

(52) U.S. Cl.
USPC ..... Plt./312

(58) Field of Classification Search
USPC ..... Plt./312
See application file for complete search history.

*Primary Examiner* — Kent L Bell
(74) *Attorney, Agent, or Firm* — Buchanan Ingersoll & Rooney PC

(57) ABSTRACT

A new and distinct *Hemerocallis* cultivar of the dormant type is provided. The new cultivar is very floriferous and forms attractive ruffled bright orange flowers with a deeper orange eyezone displaying substantial substance, and a funnel-shaped form over an extended period of time. In U.S.D.A. Hardiness Zone No. 6, blooming commonly begins during June and commonly ends during mid-September. The new cultivar displays a plurality of fans and a plurality of scapes per fan. In excess of 20 buds commonly are formed per scape. The new cultivar is well suited for growing as distinctive colorful ornamentation in the landscape.

4 Drawing Sheets

Figure 1:
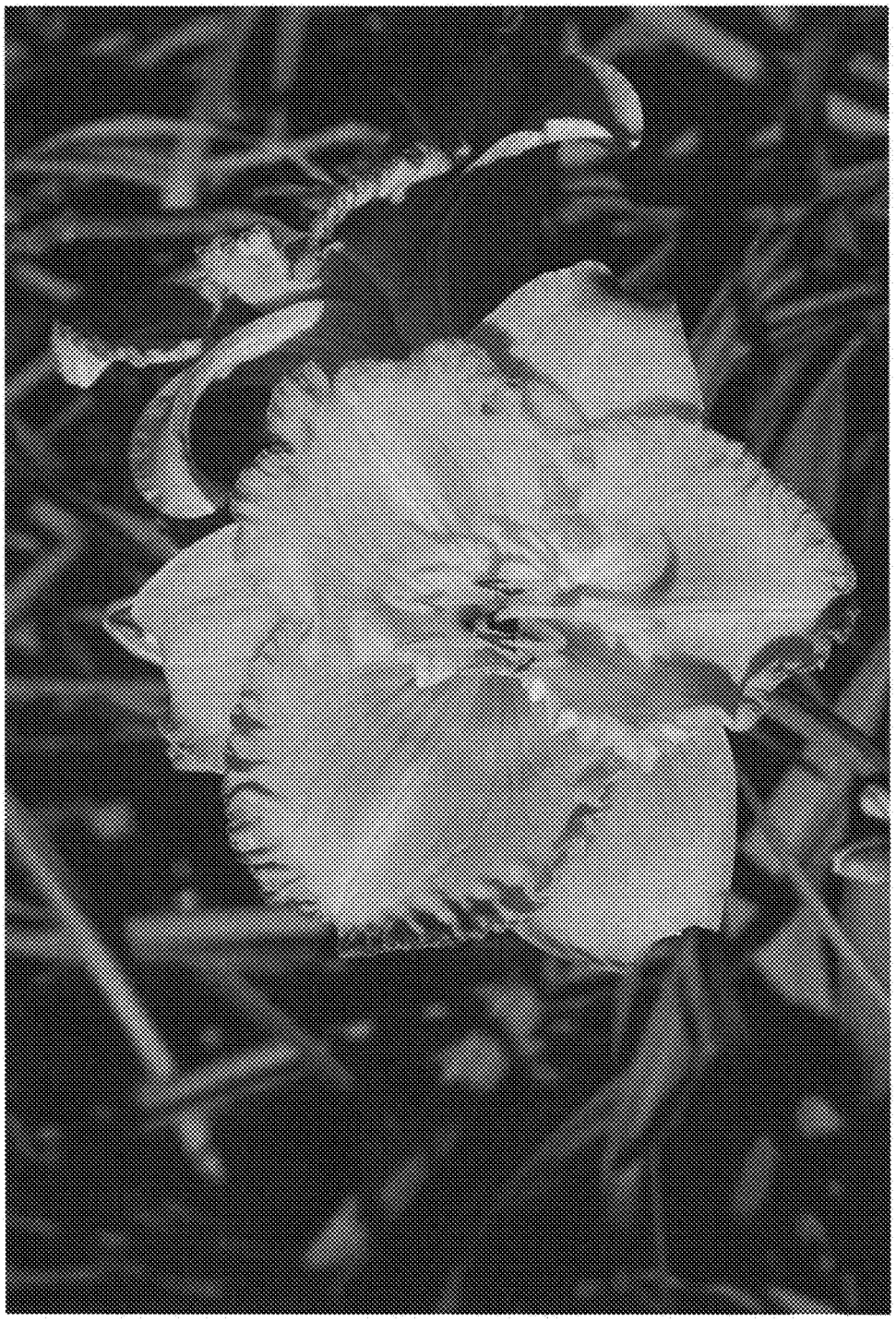
Figure 2:
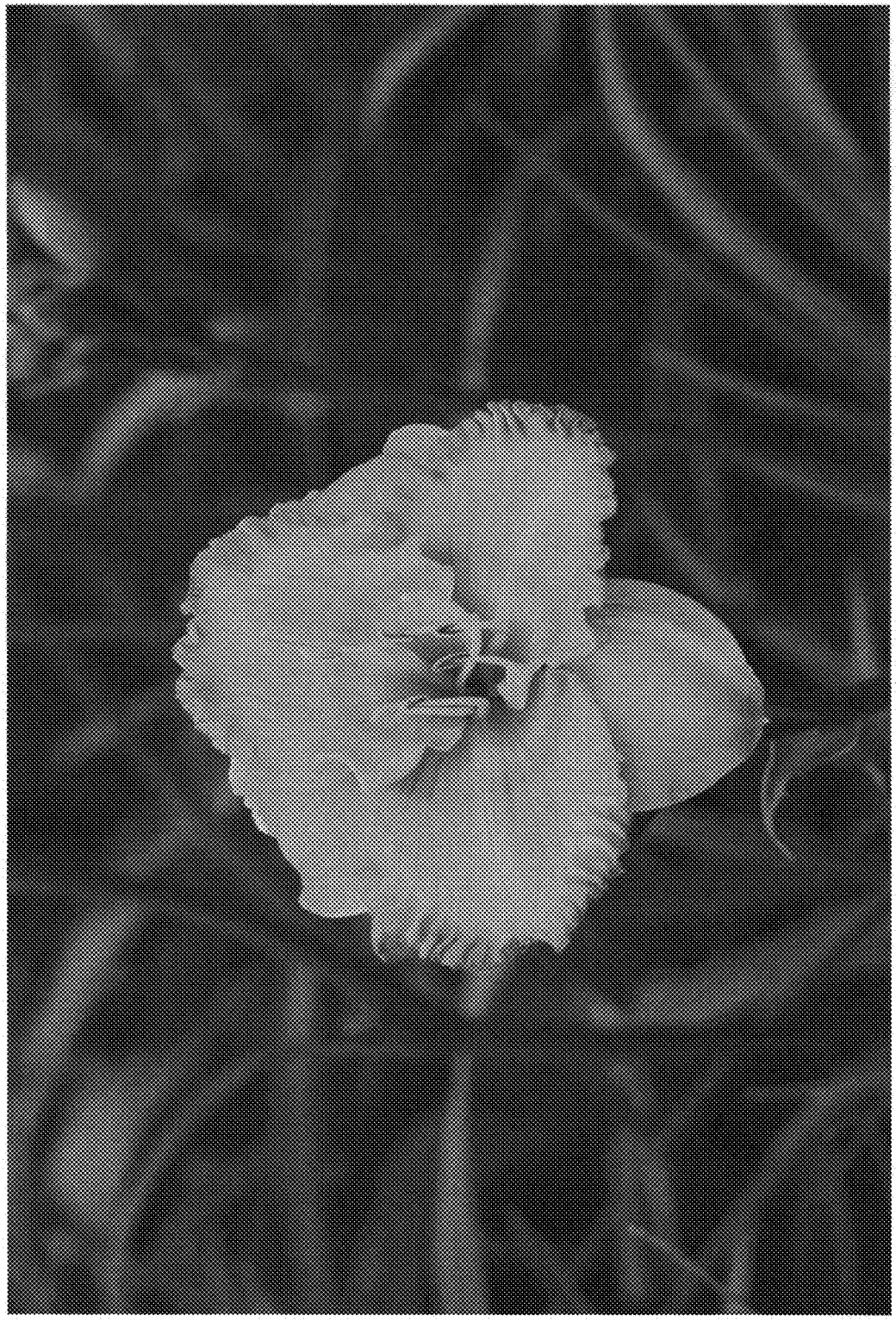
Figure 3:
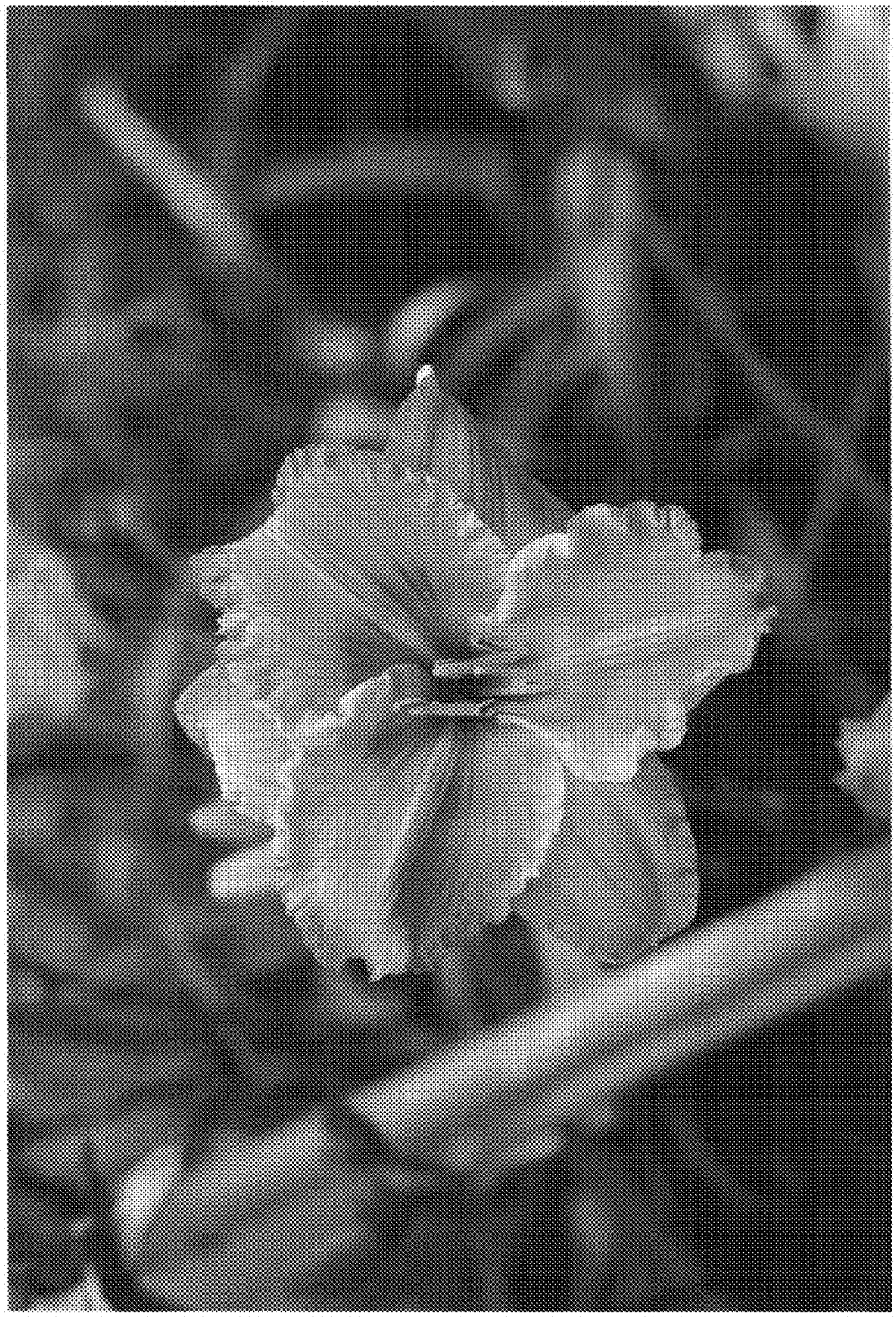

Botanical/commercial classification: *Hemerocallis hybrida*/Daylily.

Varietal denomination: cv. Centerton One.

SUMMARY OF THE INVENTION

The present invention comprises a new and distinct cultivar of *Hemerocallis* plant of the dormant type, and hereinafter is referred to by the cultivar name 'Centerton One'.

The new cultivar is the product of a planned breeding program which had as its objective the creation of a new Daylily cultivar that is intended for use as attractive ornamentation in the landscape.

The cross that resulted in the production of the new cultivar of the present invention was carried out in a controlled environment during May, 1999, at Bridgeton, N.J., U.S.A. The female parent (i.e., the seed parent) of the new cultivar was the 'Indy Inca's Gold' cultivar (non-patented in the United States) which displays golden yellow flowers of less than optimum substance.

The male parent (i.e., the pollen parent) of the new cultivar was the 'Brazilian Coral' cultivar (non-patented in the United States) which displays coral/red flowers of less than optimum substance. Each of the parent plants is registered with the American *Hemerocallis* Society.

The parentage of the new cultivar of the present invention can be summarized as follows:

'Indy Inca's Gold'×'Brazilian Coral'.

The seeds resulting from the above pollination were sown and small plantlets were obtained which were physically and biologically different from each other. A number of such plants were transplanted into the field at Bridgeton, N.J., U.S.A., during June 2000. Selective study during May-June 2001 resulted in the identification of a single plant of the new cultivar.

It was found that the new *Hemerocallis* plant of the present invention is of the dormant type and:

(a) forms attractive ruffled bright orange flowers with a deeper orange eyezone having substantial substance, and a funnel-shaped form,
(b) possesses a long blooming season with substantially multiple repeat blooming,
(c) exhibits a propensity to readily display a plurality of fans,
(d) readily forms a plurality of scapes per fan over the flowering season, and
(e) commonly forms in excess of 20 buds per scape.

The 'Centerton One' cultivar resembles some well-known cultivars, such as the 'Stella D' Oro' cultivar (non-patented in the United States) and the 'Happy Returns' cultivar (non-patented in the United States) in the sense that it commonly possesses an unusually long and substantially continuous blooming season (i.e., a multiple repeat character) of up to approximately 80 days in U.S.D.A. Hardiness Zone No. 6. Such blooming commonly begins during June and commonly ends during mid-September. This compares to a bloom period of less than about 30 days for over 99 percent of the hybrid Daylilies that are available in the trade.

As indicated, the 'Centerton One' plant exhibits attractive ruffled bright orange flowers with deeper orange eyezone. Such flowers can be readily distinguished from the orange-yellow flowers of the 'Stella D' Oro' cultivar, and the medium yellow flowers of the 'Happy Returns' cultivar. To the best knowledge of the originator, the 'Centerton One' cultivar is the first long and substantially continuously blooming Daylily having flowers that exhibit such a bright orange hue combined with substantial substance.

The new cultivar can form up to 5 or more fans per year. This compares to approximately 6 to 8 fans per year for the 'Stella D' Oro' cultivar and the 'Happy Returns' cultivar. Most Daylily cultivars form only approximately 2 to 3 fans per year. Also, the new cultivar commonly forms several scapes per fan during the flowering season, unlike most Daylilies that commonly produce only one scape per fan.

Asexual reproduction of the new cultivar by division was initially carried out on Sep. 1, 2001 at Bridgeton, N.J., U.S.A. At the time of such asexual reproduction the original plant of the new cultivar consisted of a clump of five fans that were phenotypically identical to each other. More specifically, the clump of the new cultivar was removed from the field and the fans were divided. It has been demonstrated that the characteristics of the new cultivar are firmly fixed and are well retained following this asexual reproduction.

The 'Centerton One' plant has not been observed under all possible environmental conditions to date. Accordingly, it is possible that the phenotype may vary somewhat with variations in the environment, such as temperature, light, day length, contact with pesticides, etc.

The new 'Centerton One' cultivar will be marketed by the Assignee under the JERSEY EARLYBIRD trademark beginning in May, 2012.

BRIEF DESCRIPTION OF THE PHOTOGRAPHS

The accompanying FIG. 1, FIG. 2, FIG. 3, and FIG. 4 show the original plant of the new cultivar in color as nearly true as it is possible to make the same in color illustrations of this character. Each photograph was obtained during early- to mid-June, beginning in 2007 and ending in 2011 while the plant was being grown either in the field or in a greenhouse at Bridgeton, N.J., U.S.A. The attractive ruffled bright orange flowers with a deeper orange eyezone in various stages of development are illustrated as well as foliage, unopened floral buds, stamens, and pistil.

DETAILED DESCRIPTION

The chart used in the identification of the colors described herein is The R.H.S. Colour Chart of The Royal Horticultural Society, London, England. In some instances, more common color terms are provided and are to be accorded their usual dictionary significance. The original plant of the new cultivar is described, except as otherwise indicated, when observed during August 2011 while growing at Bridgeton, N.J., U.S.A. under field growing conditions.

Classification:

*Botanical.*—*Hemerocallis hybrida.*

*Commercial name.*—Daylily.

*Cultivar.*—'Centerton One'.

Plant:

*Height.*—Approximately 51 cm at an age of one year.

*Width.*—Approximately 62 cm at an age of one year.

*Foliage.*—Form: single stem, substantially erect fan-shaped plant having narrow arching, long, keeled, grass-like glabrous slightly textured sessile leaves that are two-ranked at the base of the scape. Quantity: abundant, with a mature plant commonly having approximately 16 leaves per fan. Leaf Size: commonly approximately 1.75 cm in width on average, and approximately 49.5 cm in length on average. Leaf Shape: linear and long-keeled with entire margins, sharply acuminate at the apex, and slightly wider and thicker at the base. Leaf Venation: on the upper surface commonly not distinguishable, and on the under surface strongly keeled at the mid-rib and near Yellow-Green Group 147A in coloration. Texture: glabrous. Color: Yellow-Green Group 146A on the upper and under surfaces, and fading to near white just below the surface of the ground. Type: dormant with the plant commonly retaining some green coloration during the winter in U.S.D.A. Hardiness Zone No. 6b.

*Scape.*—Color: Yellow-Green Group 137B. Length: commonly approximately 51 cm on average. Diameter: commonly approximately 6 mm on average.

*Disease resistance.*—Typical of *Hemerocallis* with no problems having been observed to date.

Figure 4:
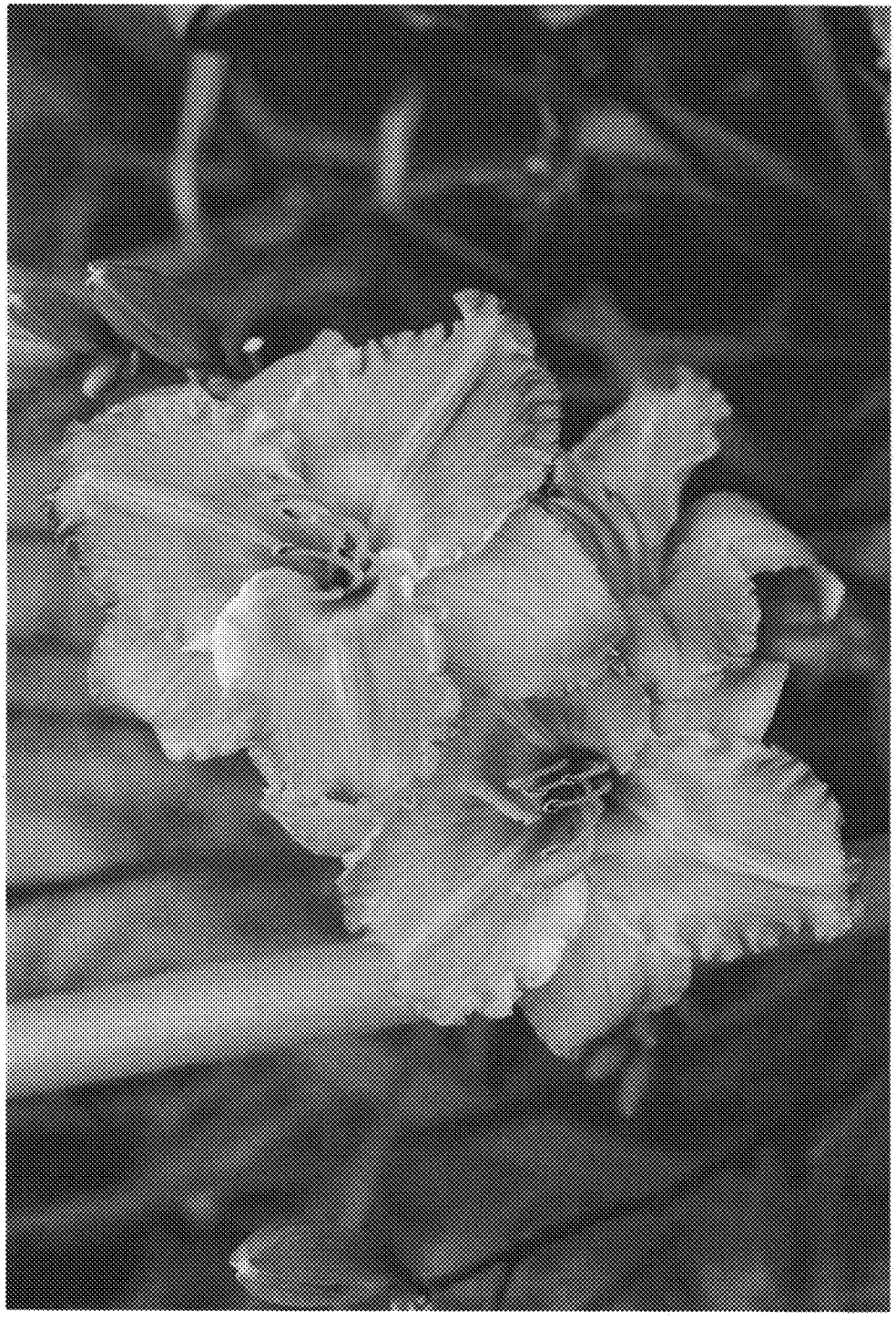

Inflorescence:

*Bud.*—Form: modified oblanceolate (as illustrated in FIG. 4), slightly tapered cylindrical with a rounded upper quarter that comes to a point. Size: on the day prior to opening commonly approximately 6.5 cm in length on average, and approximately 2 cm in width on average. Color: Yellow-Green Group 145A. Opening Rate: commonly approximately three hours on average.

*Peduncle.*—Length: commonly approximately 5 mm on average. Diameter: commonly approximately 7 mm on average. Character: rigid and sturdy. Color: near Green Group 143A.

*Pedicel.*—Length: commonly approximately 25 mm on average. Diameter: commonly approximately 5 mm on average. Color: near Green Group 138A.

*Flower.*—Size: commonly has a diameter of approximately 12.5 cm on average and a depth of approximately 8 cm on average. Borne: singly on the branchlets of a sturdy erect rachis which is ramulose. The perianth is funnel-shaped to bell-shaped with the tube widely expanding upward. Each scape commonly has at least 20 peduncles, each of which divides into approximately 2 pedicels. Blooms Per Scape: commonly approximately 1 or 2 each day. Tepalage: each flower consists of six perianth segments wherein there are three outer tepals and three inner tepals all in an imbricated arrangement. Outer Tepal Shape: wide-spreading, oblanceolate with non-ruffled slightly undulated entire margins, an acuminate apex, and a decurrent base. Outer Tepal Texture: slightly ribbed. Outer Tepal Size: commonly approximately 6.5 cm in length on average and approximately 3.5 cm in width on average. Outer Tepal Color: on the upper surface the overall area is Orange Group 28B, and the base is Yellow-Green Group 151A, and on the under surface the overall area is Yellow-Orange Group 22A, and the base is Yellow-Green Group 152C. Inner Tepal Texture: pie crust ruffled edge at margin. Inner Tepal Shape: generally elliptical, rounded at the apex, and decurrent at the base. Inner Tepal Size: commonly approximately 6.5 cm in length on average and approximately 5 cm in width on average. Inner Tepal Color: on the upper surface the overall area is Orange Group 25A, and the base is Yellow-Green Group 151A, and on the under surface the overall area is Yellow-Orange Group 22A, and the base is Yellow-Orange Group 20A. Inner Tepal Eyezone: on the upper and under surface approximately 0.75 cm in width on average, and a deeper Orange-Red Group 32A in coloration (as illustrated). Blooming Habit: the flowers commonly bloom substantially continuously and the scape commonly is substantially continuously in bloom for up to approximately 80 days per year in Hardiness Zone No. 6. Effects of Weather: the flowers will withstand rain damage in view of the strength of the tepals. Lasting Quality: commonly at least 16 hours. As with other *Hemerocallis* cultivars known to the inventor, the flower color eventually fades somewhat during the day with the natural effects of environmental conditions and ongoing maturity. Fragrance: none.

*Reproductive organs*.—Stamen Number: six per flower. Stamen Disposition: individually inserted at the summit of the perianth tube. Anther Disposition: introrse. Anther Size: approximately 5 mm in length. Anther Color: Black Group 202B. Filament Configuration: slender. Filament Length: commonly approximately 4.5 cm on average. Filament Color: Yellow-Orange Group 20A. Pollen Color: Yellow-Orange Group 23A. Pistil Number: one per flower. Style Length: approximately 6.5 cm on average. Style Color: Yellow-Orange Group 22C. Stigma Color: Yellow-Orange Group 22D. Ovaries: three-celled, oblong, and becoming a loculicidal three-valved capsule, Yellow-Green Group 144B on the outer layer and near white at the center.

*Fruit*.—Configuration: the seed pod is in the form of an ovoid capsule. Color: at maturity commonly is Yellow-Green Group 146A. Fertility: the seeds are fertile. Seed Number: typically more than 18. Seed Shape: commonly somewhat egg-shaped with the shape being influenced by the seed number within a given seed pod with the seeds becoming somewhat flattened when present in large quantity within the confined space. Seed Length: commonly approximately 5 mm on average. Seed Diameter: commonly approximately 4 mm on average. Seed Color: near Black Group 203C.

Hardiness: Cold tolerance is displayed in U.S.D.A. Hardiness Zone Nos. 4a through 8b, and heat tolerance is displayed in U.S.D.A. Hardiness Zone No. 8b.

I claim:

1. A new and distinct cultivar of *Hemerocallis* plant of the dormant type, substantially as herein shown and described, which:

(a) forms attractive ruffled bright orange flowers with a deeper orange eyezone having substantial substance, and a funnel-shaped form, (b) possesses a long blooming season with substantially multiple repeat blooming, (c) exhibits a propensity to readily display a plurality of fans, (d) readily forms a plurality of scapes per fan over the flowering season, and (e) commonly forms in excess of 20 buds per scape;

substantially as illustrated and described.

* * * * *